United States Patent [19]

Hallen

[11] 4,042,287

[45] Aug. 16, 1977

[54] SERVICE UNIT, PARTICULARLY FOR A DOCTOR'S OR A DENTIST'S OFFICE

[76] Inventor: Jan-Åke Hallen, Brinketorpsvägen 3, Partille, Sweden, 43300

[21] Appl. No.: 560,648

[22] Filed: Mar. 21, 1975

[30] Foreign Application Priority Data

Mar. 25, 1974 Sweden .................. 7403958

[51] Int. Cl.² .................. A47B 53/00; A47B 49/00
[52] U.S. Cl. .................. 312/209; 312/202; 312/252; 312/254
[58] Field of Search .............. 312/209, 254, 198, 197, 312/252, 202; 32/22; 248/356

[56] References Cited

U.S. PATENT DOCUMENTS

| | | | |
|---|---|---|---|
| 623,396 | 4/1899 | Crowder | 312/202 |
| 781,633 | 2/1905 | Conner et al. | 312/254 |
| 1,008,754 | 11/1911 | Thompson | 312/254 |
| 1,123,882 | 1/1915 | Jensen | 248/356 |
| 1,138,913 | 5/1915 | Tinsley | 312/252 |
| 1,929,677 | 10/1933 | Davis | 312/202 |
| 2,211,666 | 8/1940 | Maiben | 312/198 |
| 2,261,514 | 11/1941 | Dunigan | 312/252 |
| 2,711,741 | 6/1955 | Wassell | 312/252 |
| 3,143,331 | 8/1964 | Corey | 248/356 |
| 3,271,859 | 9/1966 | Horowitz et al. | 312/209 |
| 3,304,609 | 2/1967 | Horowitz et al. | 312/209 |
| 3,405,985 | 10/1968 | Higer | 312/198 |
| 3,451,738 | 6/1969 | Hobson | 312/209 |
| 3,455,620 | 7/1969 | Coburn | 312/209 |

Primary Examiner—Robert L. Wolfe
Assistant Examiner—Victor N. Sakran

[57] ABSTRACT

A service unit for facilitating a doctor's or a dentist's work at treatment of a patient comprises a work bench and one or more cupboards, rotatably supported on a pillar stand with a substantially vertical axis of rotation; the pillar stand is mainly of U-shape with two shanks and an intermediate, vertical portion; the ends of the shanks, remote from said intermediate portion, being connected to/or designed as vertically extending journal supports, and said intermediate portion, and/or the shanks, being provided with two horizontal cross bars spaced apart a distance in the vertical direction and intended for carrying the work bench and the cupboards.

4 Claims, 6 Drawing Figures

SERVICE UNIT, PARTICULARLY FOR A DOCTOR'S OR A DENTIST'S OFFICE

FIELD OF THE INVENTION

This invention relates to a service unit, particularly for a doctor's or a dentist's office, for operating rooms etc., and comprising a work bench and at least one upper-cupboard arranged above the work bench, the work bench and the upper-cupboard both being rotatably carried by a pillar stand.

BACKGROUND OF THE INVENTION

When treating a patient it is a desire to have the instruments to be used during the treatment as close to the working area as possible, and also that the person performing the treatment has a comfortable working position from where he can reach all the required apparatuses and aids without rising to his feet and without making larger body movements. This desire is equal for the person performing the treatment and for his assistant.

SUMMARY OF THE INVENTION

The purpose of the present invention is to provide a service unit which satisfies these demands, and which is designed in such a way that almost all functions necessary during the treatment are collected within comfortable reach. This purpose has been solved thereby that the pillar stand includes a substantially U-shaped pillar, the vertical rotation axis of which is located at the outer ends of the U-shanks and mainly in parallel with a line through the U's middle portion situated between the U-shanks, two horizontal cross bars intended for carrying the work bench and the upper-cupboard resp. being fitted at said middle portion and/or at the U-shanks at a mutual vertical distance.

DESCRIPTION OF THE PREFERRED EMBODIMENTS

Figure 1:
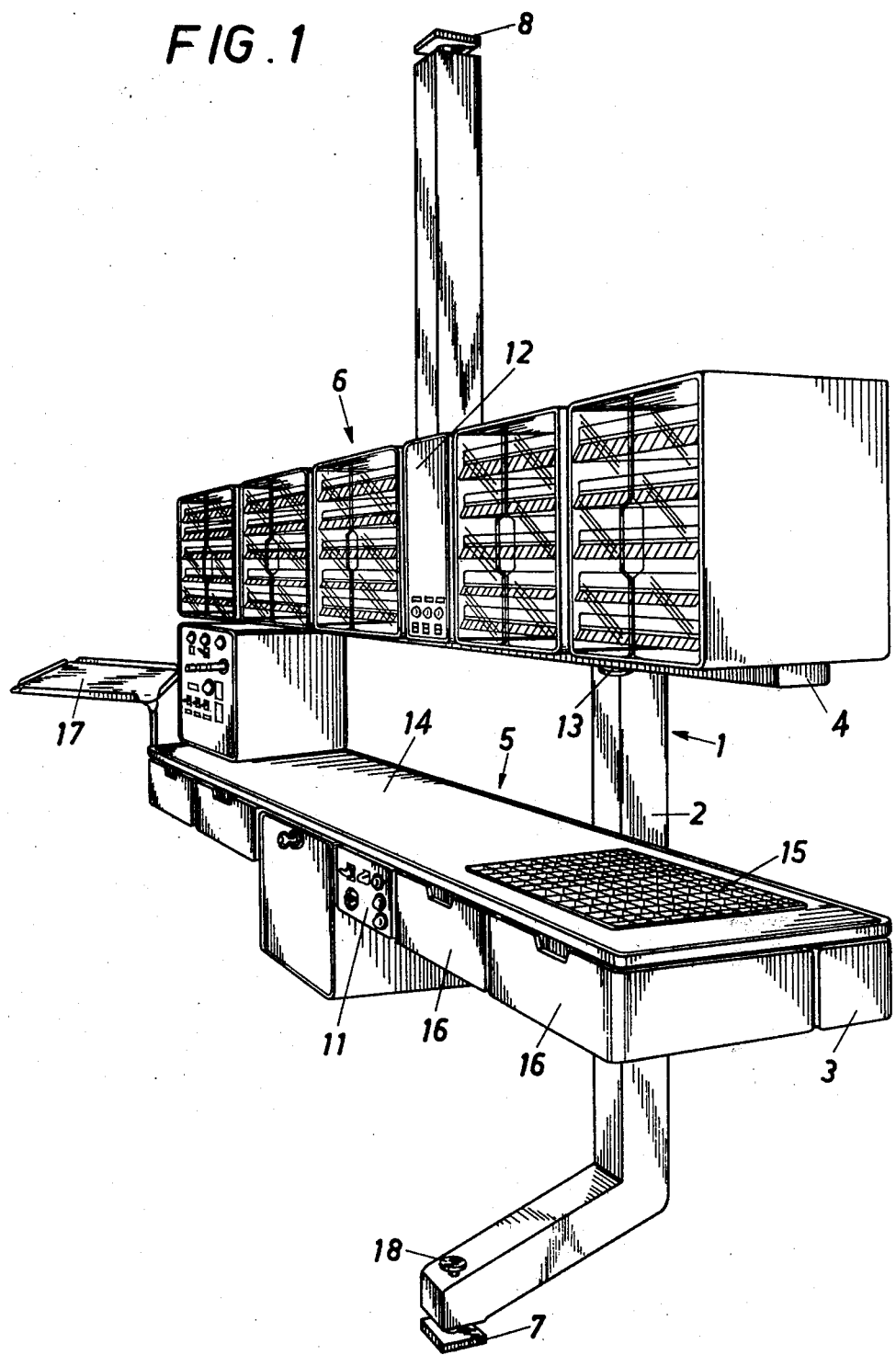
FIG. 1 shows in perspective an embodiment of the service unit according to the invention.
Figure 2:
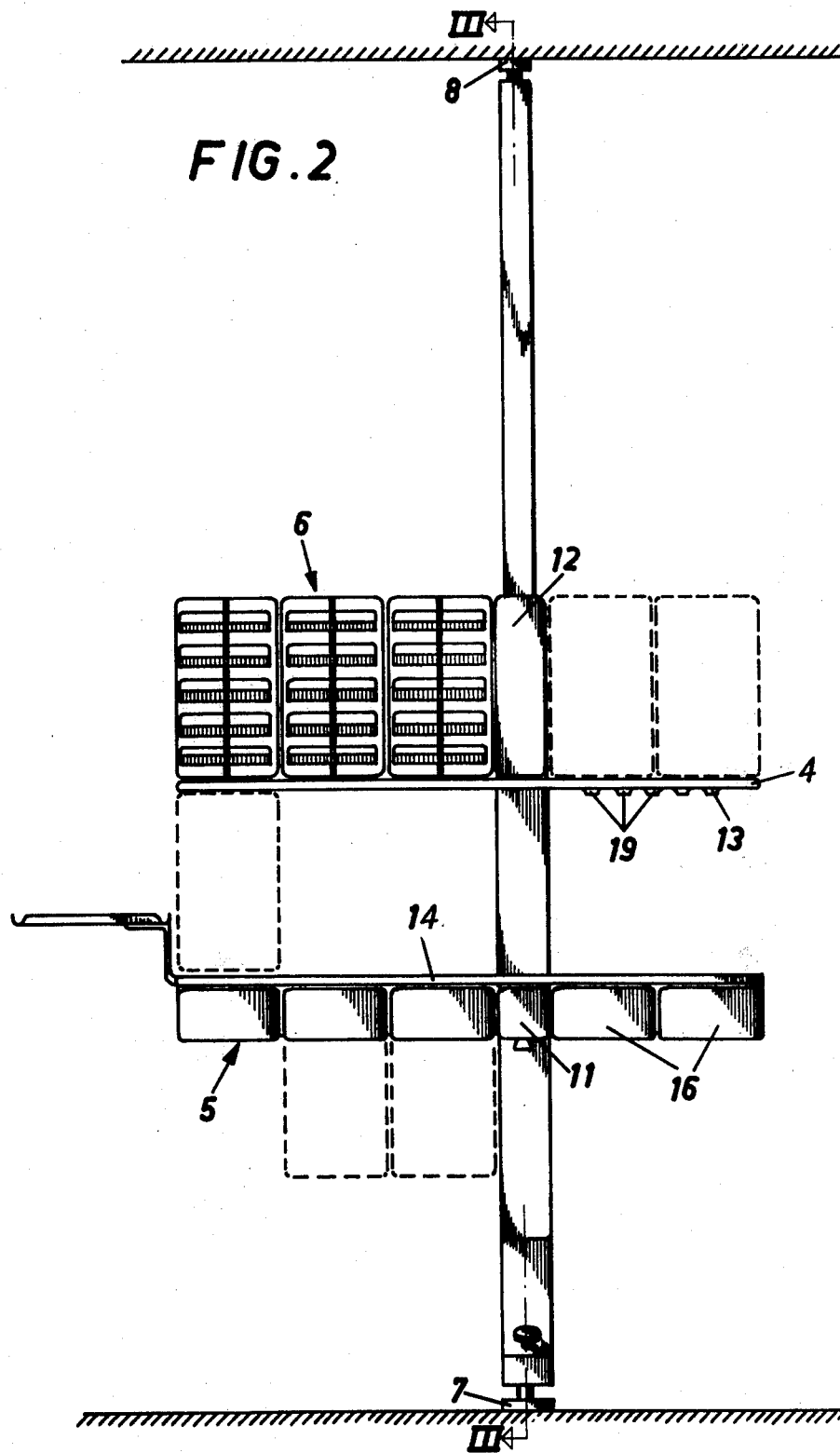
FIG. 2 shows the service unit according to FIG. 1 in a front view.

The service unit according to the invention comprises a stand 1 designed as a vertical pillar 2 and rigidly fitted thereto on a mutual distance are two horizontal, parallel cross bars 3 and 4 intended for carrying a work bench 5 and one or more upper-cupboards 6 resp.

Figure 3:
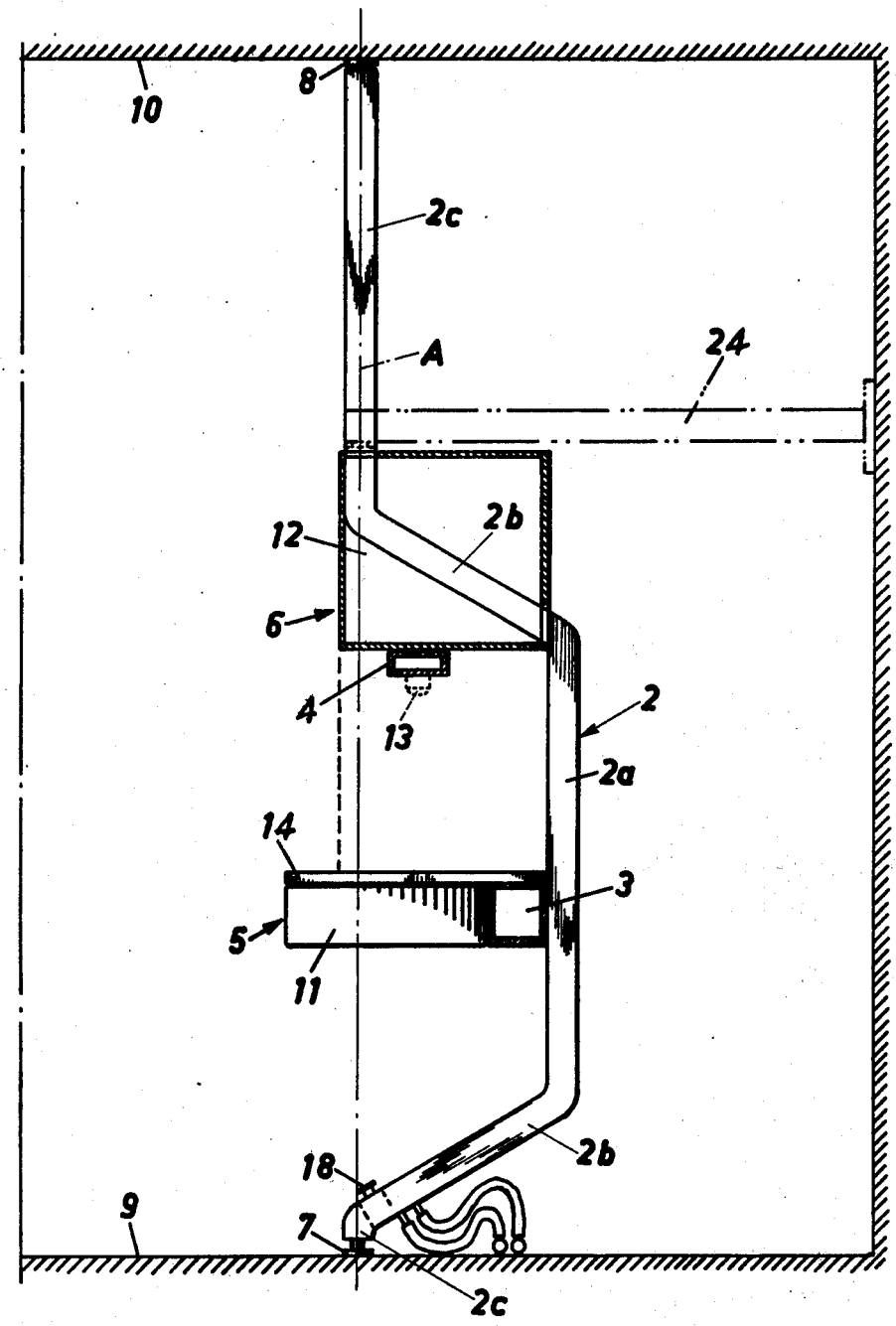
FIG. 3 is a section along line III—III in FIG. 2.
Figure 6:
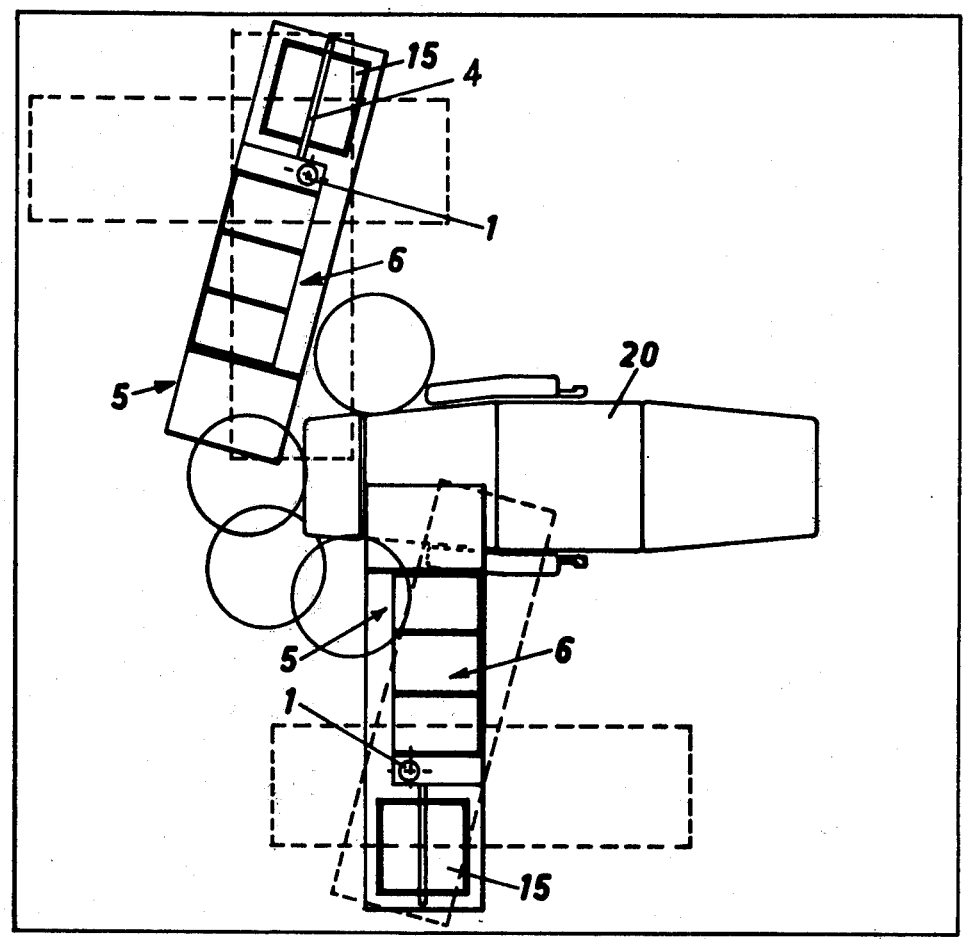
FIG. 6 shows in a schematic view from above two service units applied in a dentist's office.

The stand is at its lower end provided with a pillar base 7 and has at its upper end a top support 8, which are both designed as clamping means for enabeling the stand to be vertically arrested between two opposite surfaces, such as a floor 9 and a ceiling 10 of a room; see FIG. 3. The pillar base 7 and the top support 8 are designed in such a manner that the pillar is rotatable around a vertical axis, whereby the work bench and the upper cupboards thereabove may be pivoted for instance to a position above the patient and in direct connection to the work area so as shown in FIG. 6. By altering the relative position of work bench and cupboard between pillar base 7 and top support 8, it is possible to adjust the level above the floor of the work bench 5 and of the upper-cupboards for instance from standing to sitting level.

It can be seen best from FIG. 3 that the pillar 2 is mainly U-shaped as viewed from the side, with two U-shanks 2b and an intermediary or middle portion 2a, which is arranged vertically and in parallel with but spaced apart from the axis of rotation A. The ends of the U-shanks 2b opposite from the middle portion 2a are connected to or designed as vertical posts 2c which at their outer ends are journalled at the base 7 and at the topsupport 8, resp.

The pillar 2 as well as the cross bars 3 and 4 are hollow and the internal spaces are used for ducts for water and drainage, pressurized air conduits, lines for electricity and telephone etc. All these conduits are preferably introduced into said spaces through an aperture in the pillar just above the pillar base 7. The design of the cupboards can vary somewhat in view of the field of application, but common for all service units are two centre cupboards 11 and 12, which are parts of the supporting structure. The centre cupboard 11 preferably accomodates mixing valves and thermostat valve for an outlet pipe 13 arranged in the upper cross bar 4, whereas the upper centre cupboard 12 may contain communication apparatuses such as intercom, telephone etc. A very shallow sink 15 is arranged in the work top 14 of the work bench 5 just below the outlet pipe 13, and said sink can be equipped with a grill which prevents splashes. The sink 15 is so low that the drawers 16 therebelow will have full height. For the purpose of connecting different electric apparatuses there is arranged at the rear of the work bench, for instance inside the cross bar 3, a number of contacts for low tension and high tension current, and possibly also connections for pressurized air, oxygen etc.

The work bench and the upper-cupboards are preferably designed to extend further on one side of the pillar than on the other side, and the longer side may be equipped with a support for a pivotable tray 17, which further increases the possibilities of adaptation to different demands and wishes.

At the lower or upper end of the pillar there might be provided a device for arresting the pillar against rotation, e.g. a foot-operated button 18 or a pedal.

The upper cross bar 4 is so shaped that one or more upper-cupboards 6 can be fitted thereto, some cupboards of which may contain precomposed treatment trays whereas one cupboard is equipped with a number of containers for liquid soap, disinfectants etc, each of which containers communicate with its own discharge nozzle 19 at the lower side of cross bar 4.

An arrangement considered to be convenient at a dentist's office is shown in FIG. 6, where two service units according to the invention has been used, one on each side of the patient's chair 20. The service units are located so that they may be pivoted to optional positions above the patient's chest and/or beside the patient, the dentist thereby at his side having all the instruments and apparatuses he will need at his service unit, whereas the assistant at the other side of the patient, at the other service unit has all aids required for the assistance.

Figure 4:
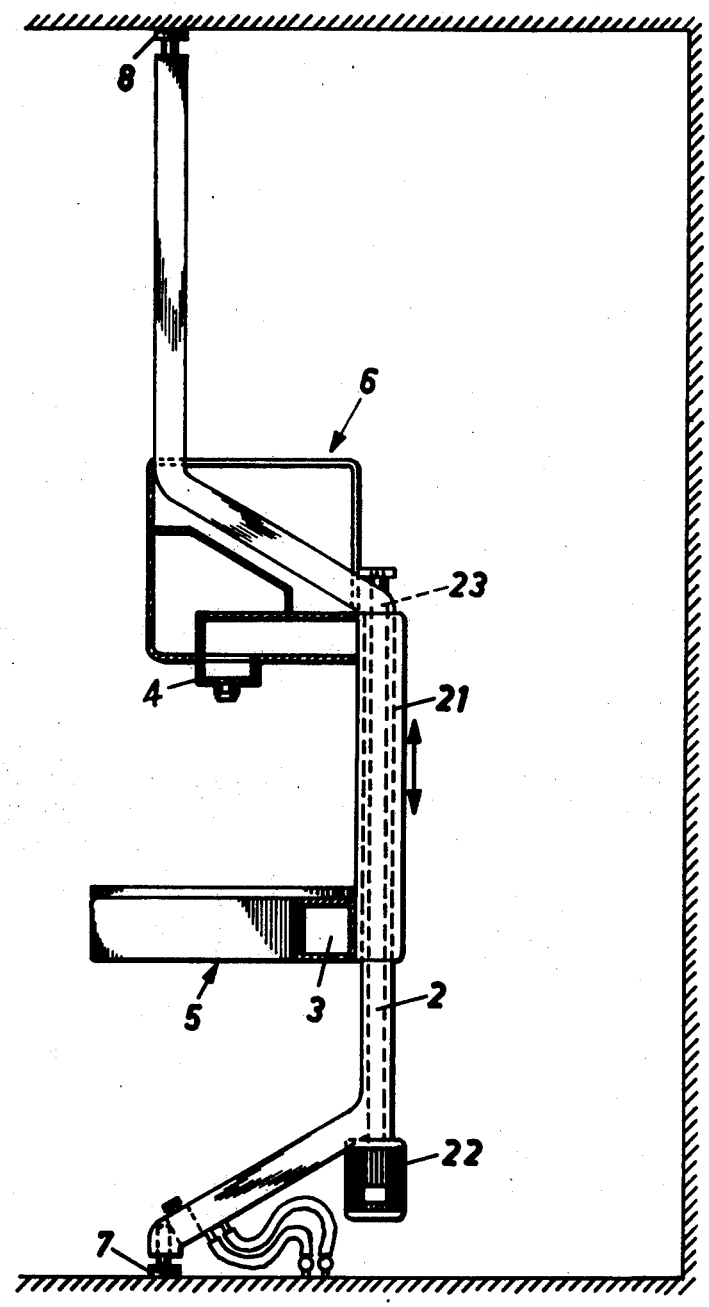
FIG. 4 shows a section through a modified embodiment of the invention.
Figure 5:
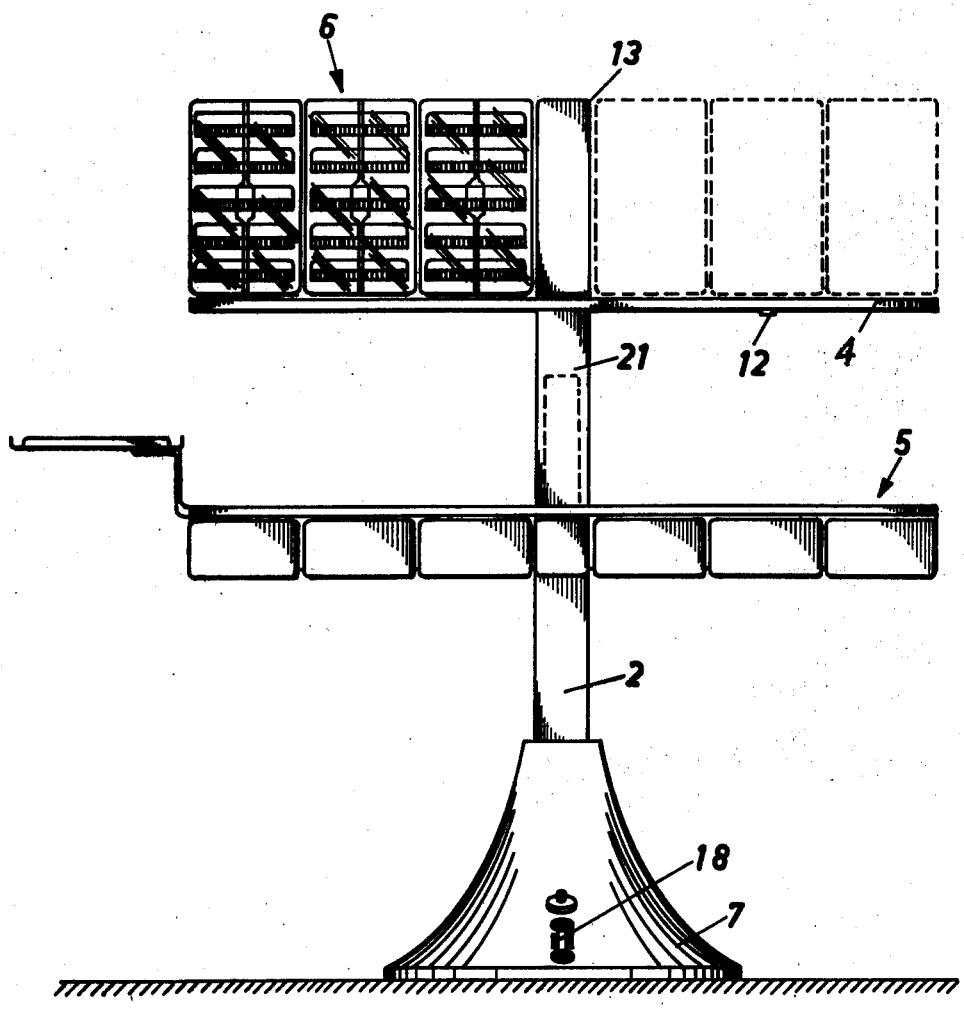
FIG. 5 is a view, similar to FIG. 2, of a further embodiment of the invention.

For certain purposes it can be convenient to be able to raise and lower the work bench and the upper-cupboards and FIGS. 4 and 5 show two such embodiments.

The cross bars 3 and 4 are at both these embodiments fixed to a column 21, which is axially displaceable along the pillar 2. The column is by suitable manually operated or motor-powered means adjustable in the vertical direction, whereby the work bench and the upper-cupboards may be raised or lowered to a convenient working level. The adjustment means may be electric motor 22, which via a transmission drives a spindle 23, provided with a longitudinal helical thread. A nut, (not shown), is arranged to be movable along the spindle under cooperation with the helical thread thereon, said nut being fixed to the column 21. Mechanical, pneumatic or hydraulic driving means may be used for this purpose instead of the electric motor.

The embodiment according to FIG. 5 differs from that according to FIG. 4 in that the pillar 2 is not clamped between floor and ceiling, but is instead provided with a solid pillar base 7, dimensioned to be able to absorb occuring load moments. The pillar 2 is located centrally in the work bench and the upper cupboards, but it may of course be located elsewhere, e.g. at one of the side edges.

The invention is not limited to the embodiments shown and described, but a plurality of modifications are possible within the scope of the claims. Instead of clamping the pillar stand between floor and ceiling the stand may for instance be fixed at its upper end by a horizontal bracket 24, which is fitted to an adjacent wall; see FIG. 3.

What I claim is:

1. A dental service unit comprising in combination a U-shaped pillar stand, a workbench and at least one upper cupboard arranged above said workbench, each of said workbench and said one cupboard being fixedly-mounted on intermediate portions of said U-shaped pillar stand, the pillar stand including a vertical rotation axis located at outer ends of vertically spaced legs of said pillar stand, said vertical rotation axis extending generally through forward portions of said workbench and cupboard, said pillar stand including an intermediate portion substantially parallel to said vertically spaced legs and connected thereto by vertically spaced, lateral support portions, said work table projecting forwardly from said last-mentioned intermediate portion and said cupboard being mounted on the uppermost lateral portion, said vertically spaced legs of said pillar stand including support elements for respectively engaging vertically spaced support surfaces for maintaining said pillar stand in a relatively fixed position with respect to the vertically spaced support surfaces, said pillar stand being tubular and said vertically spaced lateral portions comprising hollow sections, inside which sections and pillar stand are arranged distrubution service ducts for water, drainage, and supply lines for air, electricity, telephone service, and the like.

2. A dental service unit as set forth in claim 1, in which the pillar stand legs include clamping means for clamping the pillar stand in vertically extending relationship between two vertically spaced, fixed surfaces.

3. A dental service unit as set forth in claim 1, in which said vertically spaced, lateral portions, workbench and cupboard include means for vertically adjusting the table and cupboard as a unit with respect to said pillar stand.

4. A service unit as claimed in claim 1, in which the cross bars extend further on one side of the pillar stand than on the other side thereof.

* * * * *